(12) United States Patent
Schulze et al.

(10) Patent No.: US 6,620,161 B2
(45) Date of Patent: Sep. 16, 2003

(54) ELECTROSURGICAL INSTRUMENT WITH AN OPERATIONAL SEQUENCING ELEMENT

(75) Inventors: Dale R. Schulze, Lebanon, OH (US); Richard P. Nuchols, Loveland, OH (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/768,768

(22) Filed: Jan. 24, 2001

(65) Prior Publication Data

US 2002/0099372 A1 Jul. 25, 2002

(51) Int. Cl.[7] .............................................. A61B 18/18
(52) U.S. Cl. ............................ 606/51; 606/41; 606/45; 606/49; 606/52
(58) Field of Search ................................ 606/32, 39, 40, 606/41, 45, 46, 47, 48, 49, 50, 51, 52; 607/101

(56) References Cited

U.S. PATENT DOCUMENTS

| | | | |
|---|---|---|---|
| 2,002,594 A | 5/1935 | Wappler et al. |
| 3,844,272 A | 10/1974 | Banko |
| 4,052,980 A | 10/1977 | Grams et al. |
| 5,013,312 A | 5/1991 | Parins et al. |
| 5,324,289 A | 6/1994 | Eggers |
| D349,341 S | 8/1994 | Lichtman et al. |
| D350,606 S | 9/1994 | Koros et al. |
| 5,373,840 A | 12/1994 | Knighton |
| 5,403,312 A | 4/1995 | Yates et al. |
| 5,443,463 A | 8/1995 | Stern et al. |
| 5,445,638 A | 8/1995 | Rydell et al. |
| 5,456,684 A | 10/1995 | Schmidt et al. |
| 5,458,598 A | 10/1995 | Feinberg et al. |
| 5,462,546 A | 10/1995 | Rydell |
| 5,484,436 A | 1/1996 | Eggers et al. |
| 5,514,148 A | 5/1996 | Smith, III |
| 5,527,313 A | 6/1996 | Scott et al. |
| 5,531,744 A | 7/1996 | Nardella et al. |
| 5,569,274 A | 10/1996 | Rapacki et al. |
| 5,573,534 A | 11/1996 | Stone |
| 5,573,535 A | 11/1996 | Viklund |
| 5,665,085 A | 9/1997 | Nardella |
| 5,665,100 A | 9/1997 | Yoon |
| 5,667,480 A | 9/1997 | Knight et al. |
| 5,695,514 A | 12/1997 | Chin |
| 5,709,224 A | 1/1998 | Behl et al. |
| 5,709,680 A | 1/1998 | Yates et al. |
| 5,713,896 A | 2/1998 | Nardella |
| 5,722,934 A | 3/1998 | Knight et al. |
| 5,725,479 A | 3/1998 | Knight et al. |
| 5,766,166 A | 6/1998 | Hooven |
| 5,772,576 A | 6/1998 | Knighton et al. |
| 5,776,128 A | 7/1998 | Eggers |
| 5,792,139 A | 8/1998 | Chambers et al. |
| 5,797,938 A | 8/1998 | Paraschac et al. |
| 5,797,941 A | 8/1998 | Schulze et al. |
| 5,797,947 A | 8/1998 | Mollenauer |
| 5,800,449 A | 9/1998 | Wales |
| 5,810,128 A | 9/1998 | Eriksson et al. |

(List continued on next page.)

FOREIGN PATENT DOCUMENTS

| | | |
|---|---|---|
| WO | WO 99/12487 | 3/1999 |
| WO | 99/66850 | 3/1999 |
| WO | 99/12487 | 12/1999 |
| WO | WO 99/66850 | 12/1999 |
| WO | WO 00/15116 | 3/2000 |
| WO | WO 00/18303 | 4/2000 |

OTHER PUBLICATIONS

PCT International Search Report, dated Nov. 20, 2002, for PCT Int'l Appln. No. PCT/US02/00174.

*Primary Examiner*—Rosiland S. Kearney
(74) *Attorney, Agent, or Firm*—Brian S. Tomko

(57) ABSTRACT

A surgical instrument useful in harvesting blood vessels such as veins and arteries. The instrument has a pair of jaws and a central cutting element displaceable distally and proximally to dissect tissue contained between the jaws. A sequencing element prevents the cutting element from being engaged when the jaws are in the open configuration.

20 Claims, 10 Drawing Sheets

U.S. PATENT DOCUMENTS

| | | |
|---|---|---|
| 5,810,808 A | 9/1998 | Eggers |
| 5,817,013 A | 10/1998 | Ginn et al. |
| 5,826,776 A | 10/1998 | Schulze et al. |
| 5,827,279 A | 10/1998 | Hughett et al. |
| 5,833,690 A | 11/1998 | Yates et al. |
| 5,836,945 A | 11/1998 | Perkins |
| 5,853,417 A | 12/1998 | Fogarty et al. |
| RE36,043 E | 1/1999 | Knighton |
| 5,860,975 A | 1/1999 | Goble et al. |
| 5,876,401 A * | 3/1999 | Schulze et al. ............... 606/41 |
| 5,891,140 A | 4/1999 | Ginn et al. |
| 5,891,141 A | 4/1999 | Rydell |
| 5,913,866 A | 6/1999 | Ginn et al. |
| 5,921,984 A | 7/1999 | Sutcu et al. |
| 5,922,001 A | 7/1999 | Yoon |
| 5,925,045 A | 7/1999 | Reimels et al. |
| 5,928,135 A | 7/1999 | Knight et al. |
| 5,928,138 A | 7/1999 | Knight et al. |
| 5,951,549 A | 9/1999 | Richardson et al. |
| 5,954,720 A | 9/1999 | Wilson et al. |
| 6,024,741 A | 2/2000 | Williamson, IV et al. |
| 6,030,384 A | 2/2000 | Nezhat |
| 6,039,733 A | 3/2000 | Buysse et al. |
| 6,056,746 A | 5/2000 | Goble et al. |
| 6,059,782 A | 5/2000 | Novak et al. |
| 6,066,137 A | 5/2000 | Greep |
| 6,085,586 A | 7/2000 | Arvidson et al. |
| 6,086,586 A | 7/2000 | Hooven |
| 6,113,598 A | 9/2000 | Baker |
| 6,126,658 A | 10/2000 | Baker |
| 6,334,860 B1 | 1/2002 | Dorn |

\* cited by examiner

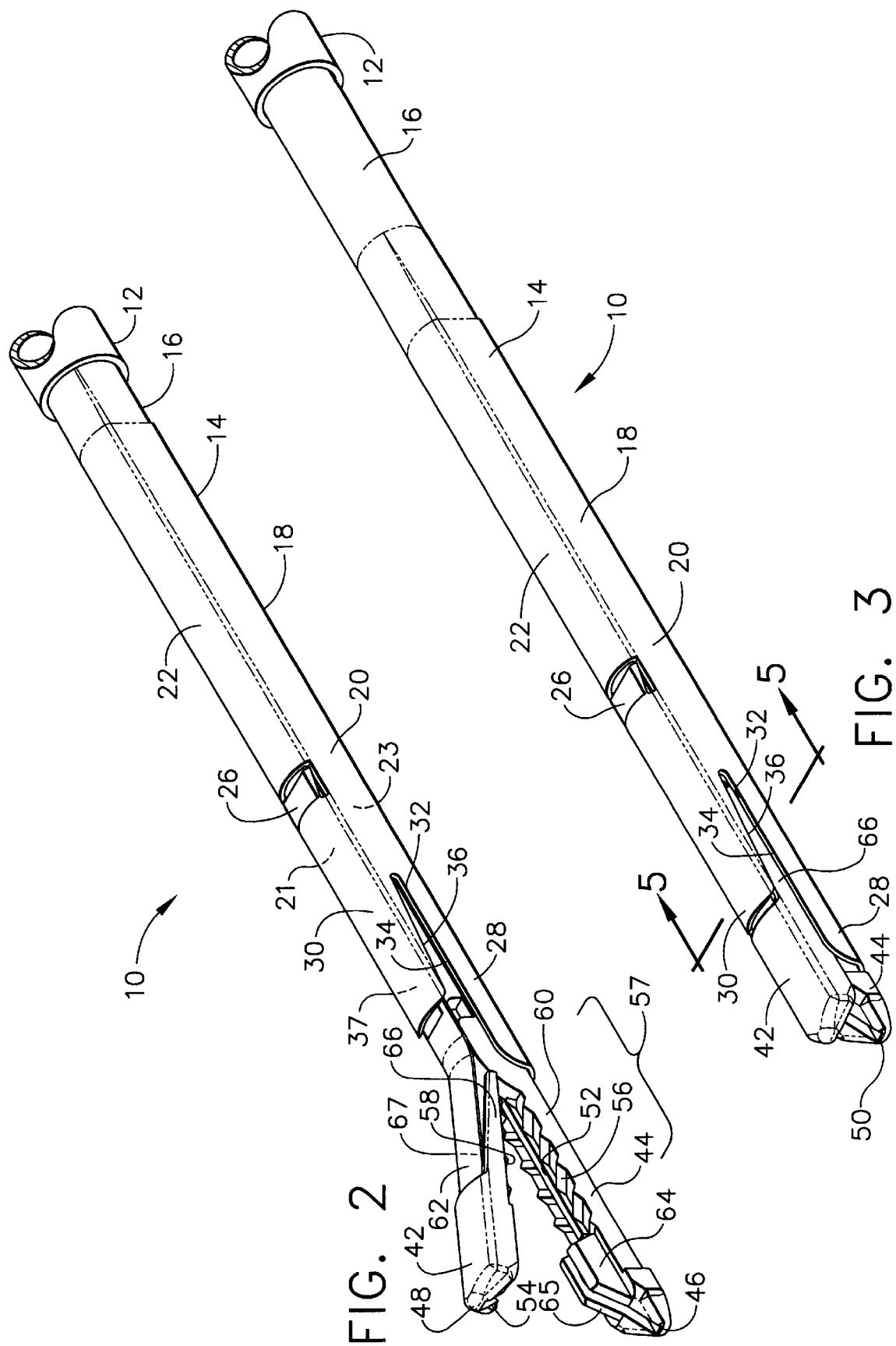

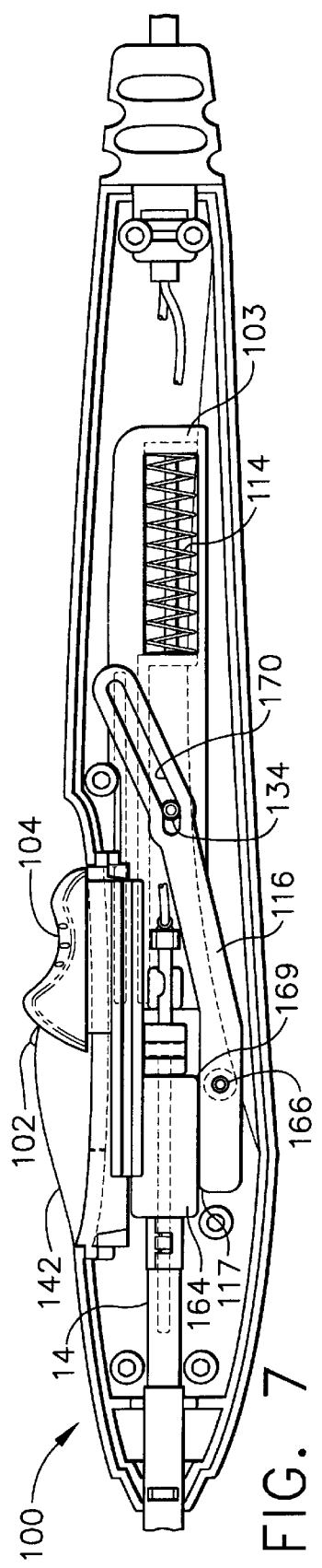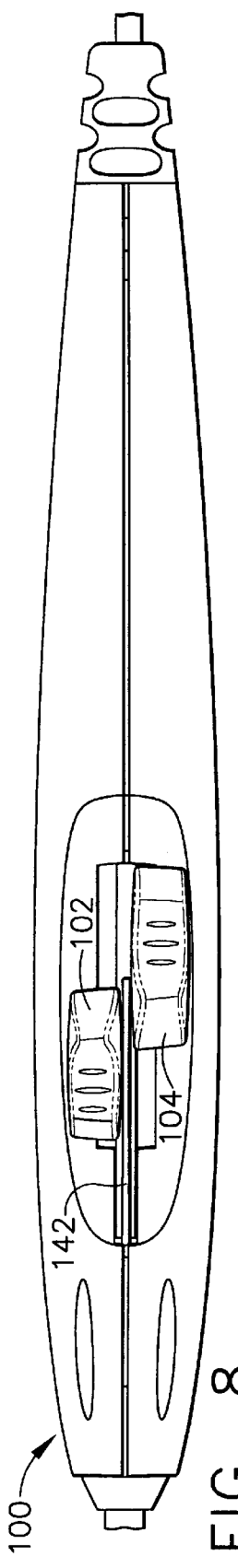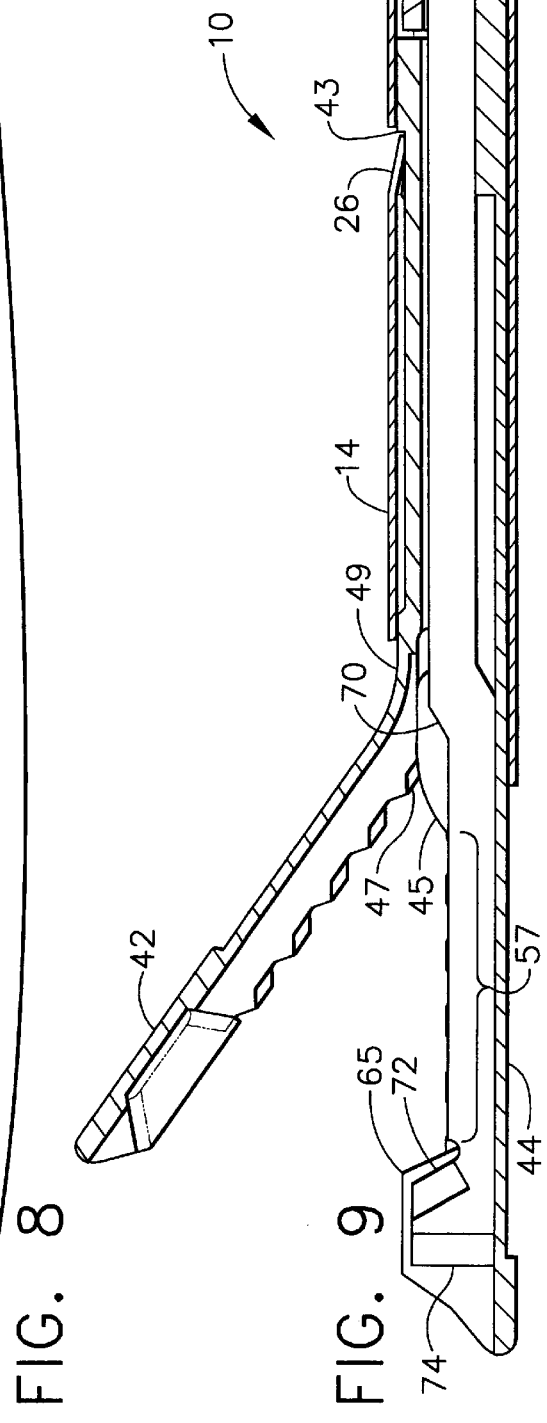

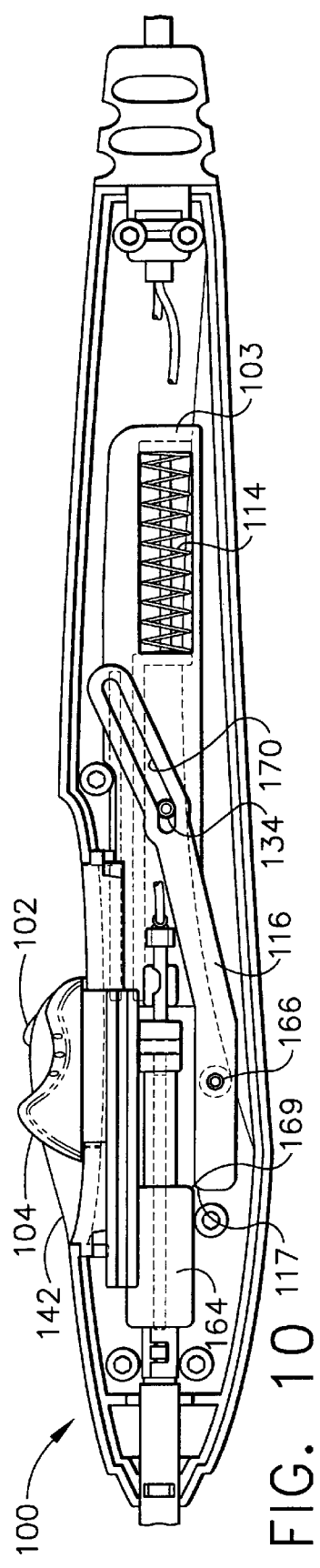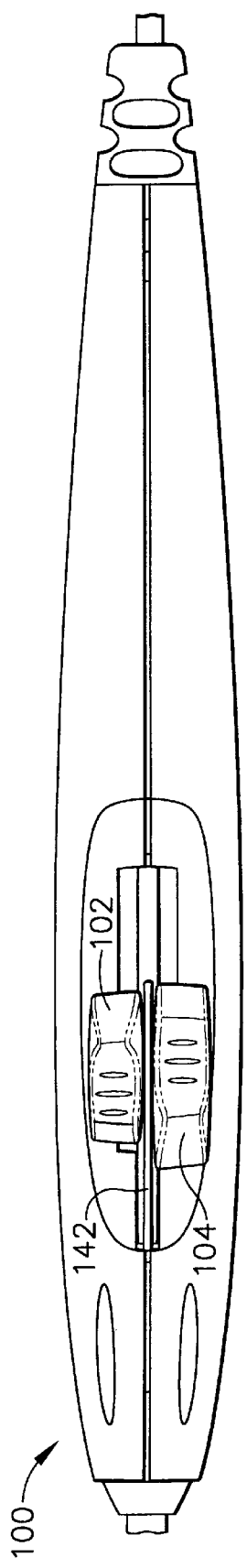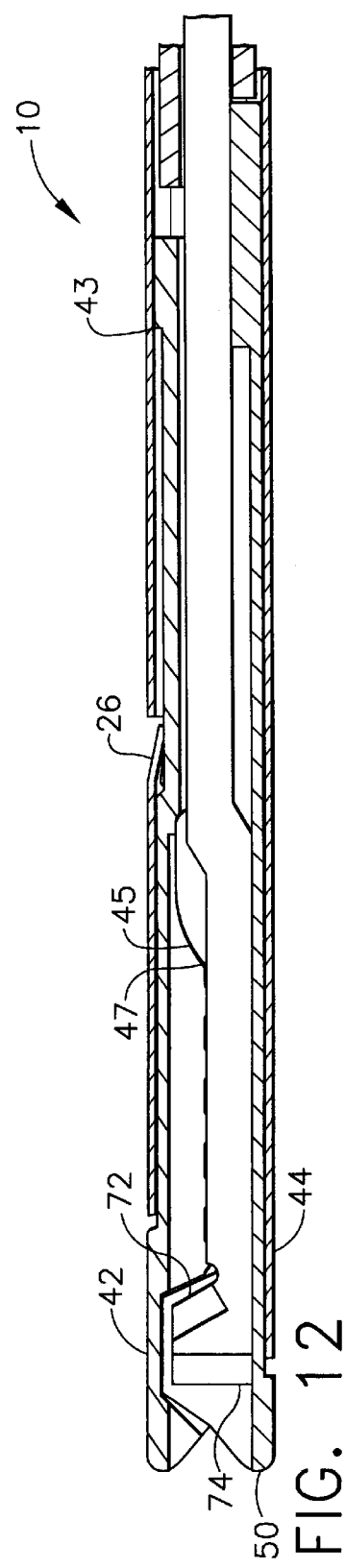

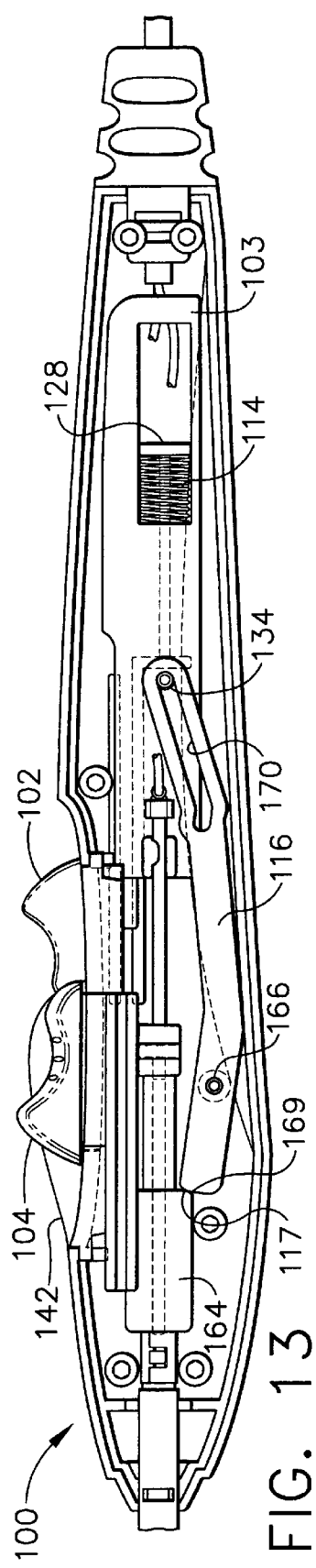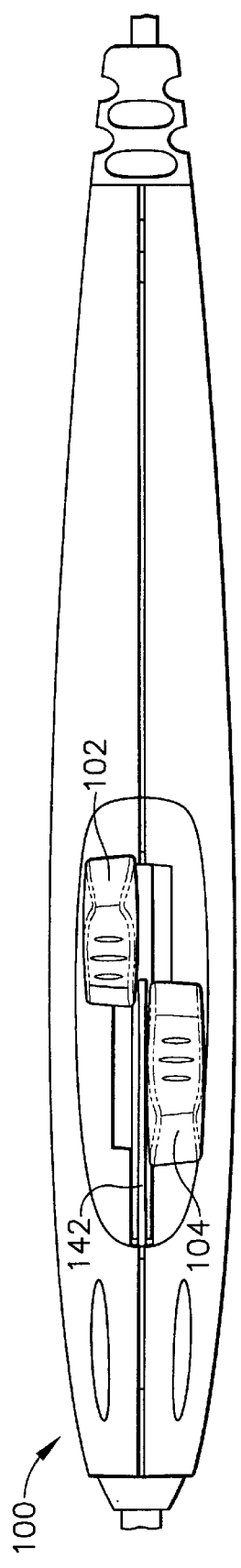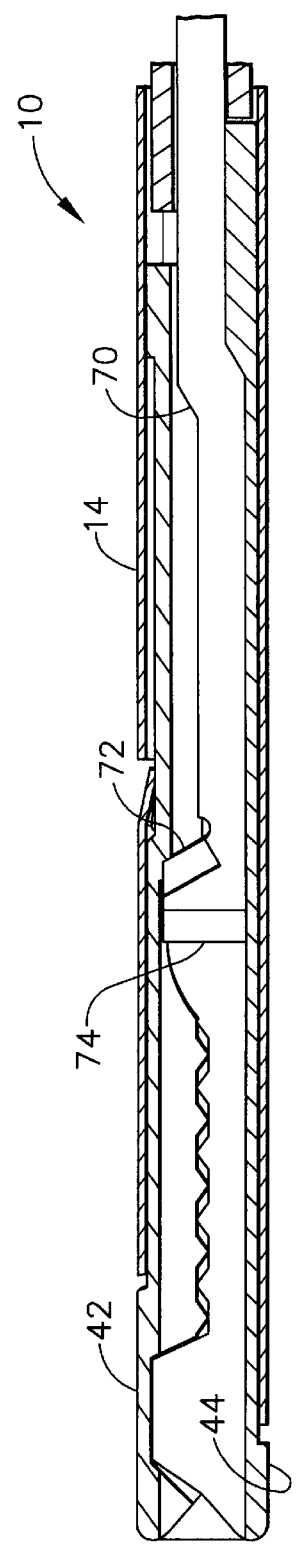

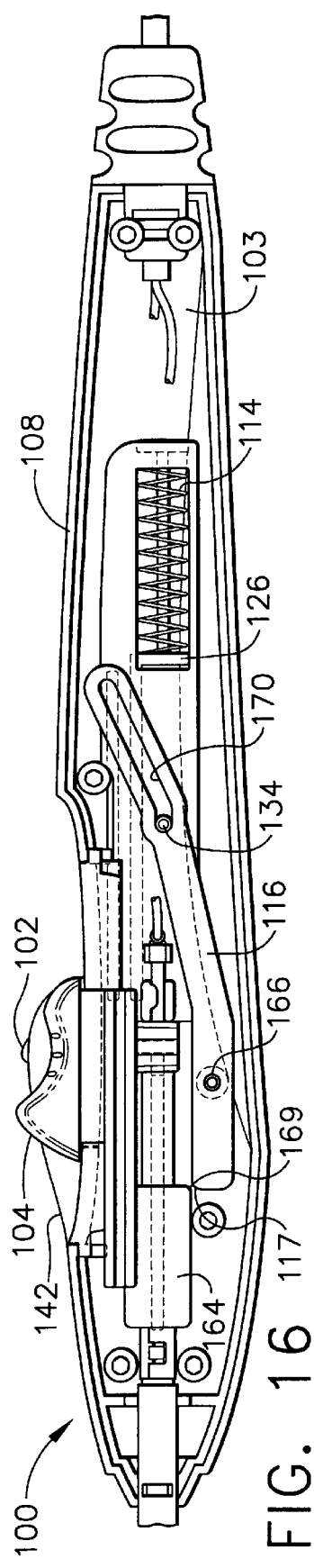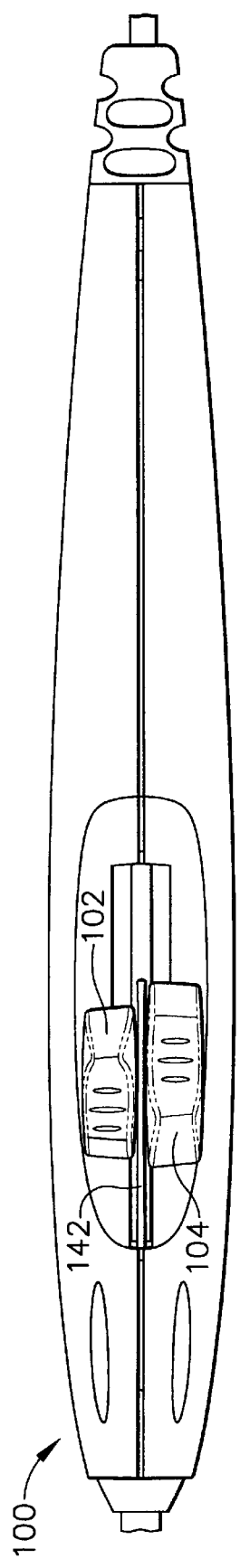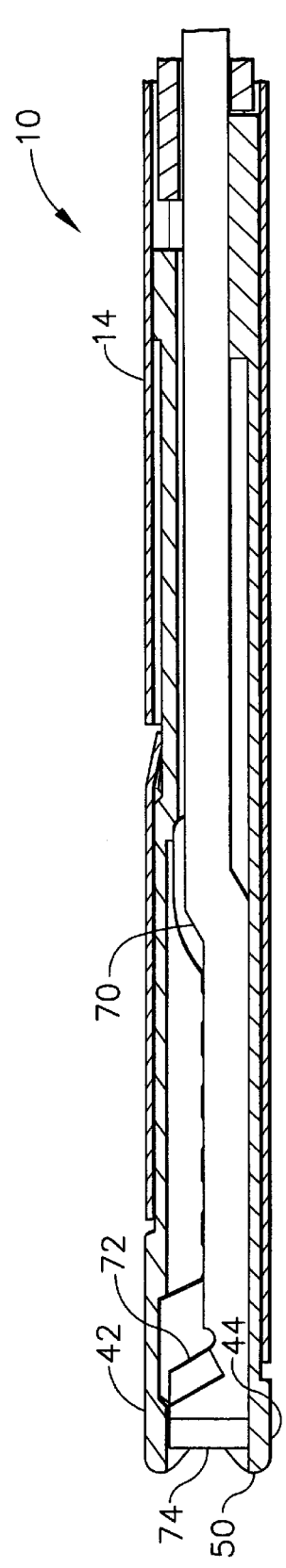

ELECTROSURGICAL INSTRUMENT WITH AN OPERATIONAL SEQUENCING ELEMENT

FIELD OF THE INVENTION

The present invention relates, in general, to bipolar electrosurgical instruments and, more particularly, to bipolar electrosurgical instruments incorporating offset electrodes.

BACKGROUND OF THE INVENTION

Surgeons and surgical assistants have been using medical devices incorporating radio frequency (RF) electricity for many years to cauterize and coagulate bodily tissues during surgical procedures. Two types of RF surgical devices are conventionally utilized: mono-polar and bipolar. Both incorporate a pair of conductors for transmission of alternating RF electricity. In a mono-polar electrosurgical instrument, a first conducting electrode having a first polarity is typically placed on the patient's skin and communicates through the body, i.e. forms a conductive path, with a second conducting electrode having the opposite polarity located on the surgical instrument. A bipolar electrosurgical instrument, however, typically incorporates both first and second electrodes of opposite polarity in the same surgical instrument, substantially restricting the flow path of electric current to tissue that is contained between the electrodes. As mentioned previously, both mono-polar and bipolar electrosurgical instruments apply RF energy through tissue. The energy is dissipated within the tissue in the form of heat due to the natural impedance of tissue. As the temperature of the tissue rises, the electrical resistivity of the tissue increases. When RF energy is applied to tissue, and as the temperature reaches about 67–70 degrees Celsius, the tissue begins to coagulate. As increasing amounts of energy dissipate in the tissue, the collagen forming the tissue matrix breaks down and appears to "melt". Mechanical compression of the coagulating tissue layers fuses and seals any contained blood vessels, so that the tissue may be cut without bleeding. When the tissue temperature reaches 100 degrees C., most fluids (including water) vaporize into the surrounding tissues and air.

The energy dissipation rate in tissue depends on numerous factors, including the inherent electrical resistivity of the tissue and the electrical current density. Electrical current density in various tissues is an important consideration in the design of the electrodes in a bipolar electrosurgical instrument, including the number, size, shape, and placement of the electrodes.

Many surgeons prefer to use bipolar electrosurgical instruments for hemostatically (without bleeding) sealing tissue prior to transection. Bipolar electrosurgical devices are known for grasping, coagulating, and cutting tissue. Typically the instruments have grasping elements, and one of the grasping elements is an electrically opposite pole of the other grasping element. For this type of conventional, bipolar electrical configuration, electrical current can be simplistically thought of as "flowing" from one grasping element (a positive pole), through the grasped tissue, and to the other grasping element (a negative pole). When tissue held between the grasping elements is coagulated, it is known that the electrical resistivity of that portion or zone of tissue increases dramatically. This causes the electrical current to seek a new path of lesser electrical resistivity around the zone, resulting in a spread to tissue adjacent to the outside of the grasping elements. Accordingly, it is believed that the zone of coagulated tissue continues to increase laterally from the grasping elements. The final width of the coagulation zone depends on several factors, including the power setting of the electrosurgical generator, and on the length of time the operator applied electrical energy to the tissue, etc. It is typical for an operator to apply electrical energy (usually by stepping on a foot actuator) for several seconds more than is actually needed to ensure that the grasped tissue is completely coagulated prior to cutting to prevent bleeding. If the amount of tissue grasped is very small, coagulation of the grasped tissue may occur so quickly that the operator cannot stop the application of electrical energy quickly enough to prevent excessive lateral spreading of the coagulation zone. In addition, the operator may not always be able to visualize the spreading of the coagulation zone because of obstructing tissue structures, especially during an endoscopic procedure; or, because the coagulation of the tissue occurs on the inside of the tissue or blood vessel.

Excessive lateral spread of the coagulation zone may be harmful to patients undergoing surgical procedures in which an organ or vessel is harvested for use in the same or a different patient. For example, in a coronary artery bypass graft (CABG) procedure, a surgeon or surgical assistant may remove a saphenous vein from one of the patient's legs to use as one or more bypass grafts on that patient's heart. In recent years, new surgical dissecting/retracting tools have been introduced to enable the surgical operator to harvest the saphenous vein endoscopically. Examples of endoscopic vessel harvesting devices and methods are contained in the following U.S. patents, which are incorporated by reference: U.S. Pat. Nos. 5,667,480; 5,722,934; 5,928,135; and 5,928,138. In such surgical procedures the operator "tunnels" with the surgical dissecting/retracting tool alongside the vein under the skin, working through a small incision made into the inside of the patient's leg or knee. The benefits of this procedure to the patient are numerous because endoscopic vein harvesting (EVH) results in greatly reduced recovery time and pain for the patient as compared to the earlier open procedure of creating an incision along the leg equal to the length of the vein harvested. In addition scarring is limited, and the incidence of serious infections reduced.

In conventional EVH procedures, the surgical operator uses the surgical dissecting/retracting tool to create a small working space at the distal end of the tool and adjacent to the vein being harvested. As the operator maneuvers the tool along the vein to separate the vein from adjacent tissues, the operator typically encounters numerous smaller collateral vascular side branches of the main vein (usually about 15). To harvest the main vein with minimal bleeding of surrounding tissues, the operator may apply at least two conventional surgical clips to each side branch encountered, using a conventional mechanical endoscopic surgical clip applier. Then the clip applier is removed, an endoscopic scissors is inserted to cut the side branch between the applied clips. Each instrument insertion and removal is not only time-consuming, but care must be taken not to cause trauma to the vein being harvested and to surrounding tissues in the leg. The operator may also use bipolar electrosurgical scissors in place of mechanical clip appliers, which are well known in the art for use in this type of surgical procedure. However, bipolar scissors may induce undesirable lateral spreading of the coagulation zone if not used correctly, and the experience of the operator is crucial in preventing injury to a harvested vein to be used in the CABG procedure. When using bipolar scissors or any of the other conventional electrosurgical instruments during an EVH procedure, the operator is required to treat each side branch at a location as far distant laterally from the main vein as practical, and the operator must apply RF energy for a minimal time to seal the side branch for cutting.

Various embodiments of a relatively new kind of bipolar, electrosurgical device are disclosed in the following patents hereinafter referred to collectively as the "offset electrode device", and are incorporated by reference herein: U.S. Pat. Nos. 5,403,312; 5,709,680; and 5,833,690. In the offset electrode device, the bipolar electrodes have an "offset" configuration and coagulation of tissue is substantially confined to only the tissue held between a pair of interfacing surfaces. The offset electrode devices also provide for high tissue compression to coagulate tissue uniformly and to force fluid out of the coagulation zone. Such fluid would vaporize during coagulation and shoot laterally from the interfacing surfaces, possibly causing thermal injury to adjoining tissue. The offset elecrode devices disclosed, however, in the referenced patents are not specifically adapted for use in endoscopic vein harvest procedures or in other types of minimally invasive surgical procedures requiring 5 mm diameter endoscopic ports. There is a need in this art for a bipolar electrosurgical instrument that may be used through a five millimeter trocar port, and that has minimally sized jaws for improved access and visualization of tissue structures in the surgical site.

Another concern of the surgical operator when using any electrosurgical instrument is the tendency of coagulated tissue to stick to the jaws of the instrument during operation of the instrument. The operator must take additional time to manipulate the instrument to release tissue adhering to the end effectors, possibly injuring surrounding tissue, especially when operating in limited working spaces during endoscopic procedures. Adhering tissue also reduces the electrical conductivity of the bipolar electrodes and it is often necessary for the operator to manually clean the electrodes in order to continue using the instrument. This is especially prevalent for forceps-type grasping instruments incorporating the conventional bipolar electrode (non-offset) configuration.

Many conventional surgical instruments incorporate cutting blades for transecting tissue held within the jaws. A potential difficulty with cutting blades of such instruments is "tissue-tagging" when the blade does not completely cut through all the tissue held in the jaws. This may occur, for example, if the cutting edge of the blade is dull or nicked. Another reason tissue-tagging may occur, or even some bleeding after the tissue is coagulated and cut, is that the tissue is not held firmly enough within the jaws of the instrument as the cutting blade is passed through the tissue held. When tissue is initially clamped within the jaws of the instrument, the clamping force may be very high due to the elasticity of the fluid-containing tissue. But after the tissue has been compressed for a period of time, and then is coagulated, most of the fluid has been driven out of the tissue, with the result that the elasticity of the tissue is greatly reduced. The clamping force on the tissue is also decreased so that the tissue may shift within the jaws as a cutting blade is passed through it. This presents the possibility that not all the tissue will be cut, or the cutting blade will pass through a portion of tissue that is not fully coagulated.

During some surgical procedures, including the EVH procedure, the surgical operator must cut and dissect a first tissue structure away from a second tissue structure prior to performing a transection or other surgical procedure on the second tissue structure. A conventional technique for this type of surgical cutting and dissecting used a pair of conventional, mechanical scissors held in an open configuration, thus forming a vee-shape with the scissors blades. The scissors blades are then advanced between the first and second tissue structures to cut and separate them. At this point, the surgical operator may remove the scissors and continue the surgical procedure with another surgical instrument such as a clip applier for ligation of the second tissue structure. During an EVH procedure, the exchange of endoscopic mechanical scissors and the clip applier in and out of the working space may occur many times, increasing the time to perform the procedure, and possibly injuring the vein or surrounding tissue. An alternative to using a mechanical scissors together with a clip applier is to use a bipolar electrosurgical scissors as described previously. Using conventional bipolar coagulation and cutting devices may result in excessive lateral spreading of the thermally affected zone of tissue, especially if the operator is inexperienced or otherwise not careful.

Another shortcoming when using currently available electrosurgical cutting instruments with cutting blades is that the cutting blade may be exposed accidentally to adjacent tissue when the operator does not intend to cut the tissue.

Accordingly, what is needed in this art is a bipolar electrosurgical instrument incorporating offset electrodes and compression zones, as described for the offset electrode device, yet improved to be less surgically invasive and to provide better access and visualization at the surgical site. There is also a need for a bipolar electrosurgical instrument that easily releases tissue from the jaws after each cycle of use, and automatically wipes electrode surfaces clean for each cycle of use. Additionally, there is a need for an instrument having more than one cutting blade that cuts through the tissue held within the jaws to improve the probability of completely transecting the tissue held, but without increasing the size or cost of the instrument. There is also a need for an instrument that provides for additional clamping force to be applied to tissue held in the jaws immediately prior to passing a cutting blade through the tissue. There is yet a further need for an instrument that safely coagulates tissue without excessive lateral thermal spread, and which reduces the need for using mechanical scissors and clip appliers during a surgical procedure. Replacing a scissors and a clip applier with a single bipolar electrosurgical cutting instrument, for example, and reducing surgery time by reducing the number of instrument exchanges during the surgical procedure, allows a significant cost savings to the hospital, and is beneficial to the patient. There is also a need for an electrosurgical instrument with a cutting blade that has an operational sequencing element that allows the movement of the cutting blade through a tissue grasping region only when the jaws are fully closed, thus reducing the possibility of accidentally injuring the patient.

SUMMARY OF THE INVENTION

Therefore, it is an object of the present invention to provide a bipolar electrosurgical instrument incorporating offset electrodes and compression zones, that is less surgically invasive and that provides better access and visualization at the surgical site.

It is another object of the present invention to provide a bipolar electrosurgical instrument that easily releases tissue from the jaws after each cycle of use, and automatically wipes electrode surfaces clean for each cycle of use.

It is yet another object of the present invention to provide an instrument having more than one cutting blade that cuts through the tissue held within the jaws to improve the probability of completely transecting the tissue held, but without increasing the size or cost of the instrument.

It is still yet another object of the present invention to provide an instrument that provides for additional clamping force to be applied to tissue held in the jaws immediately prior to passing a cutting blade through the tissue.

Yet another object of the present invention is to provide an instrument that safely coagulates tissue without excessive lateral thermal spread, and which reduces the need for using mechanical scissors and clip appliers during a surgical procedure.

Still another object of the present invention is to provide an electrosurgical instrument with a cutting blade that has an operational sequencing element that allows the movement of the cutting blade through a tissue grasping region only when the jaws are fully closed, thus reducing the possibility of accidentally injuring the patient.

Accordingly, a tissue cutting and grasping instrument is disclosed. The instrument has a handle having a proximal end, a distal end, a top and a bottom. A first actuator and a second actuator are operably mounted to the handle. There is a shaft having a distal end, a proximal end, a longitudinal axis, and a lumen therethrough. The proximal end of the shaft is mounted to the distal end of the handle. A first jaw and an opposed second jaw are mounted to the distal end of the shaft. The jaws each have a distal end and a proximal end. The distal ends of the jaws are spaced apart when the first actuator is in an open position and the distal ends of the jaws are adjacent when the first actuator is in a closed position for approximating tissue in a tissue grasping region. The jaws each have a distal dissecting member. A dissecting tip extending from the distal ends of the jaws formed by the distal dissecting members when the first actuator is in the closed position. An elongated member having a distal end, a proximal end, and a longitudinal axis. The elongated member is slidably mounted in lumen of said shaft and the proximal end of the elongated member mounted to the second actuator. A cutting element is mounted to the distal end of the elongated member. The cutting element has a first blade proximally oriented and a second blade distally oriented, such that movement of the second actuator from a central position to a proximal position causes the cutting element to move in the proximal direction wherein the first blade cuts through tissue held in the tissue grasping region between the jaws. And, further, movement of the second actuator from the proximal position to the central position causes the cutting element to move in the distal direction wherein the second blade cuts through tissue held in the tissue grasping region between the jaws. Movement of the second actuator from the central position to a distal position causes the second blade of the cutting element to extend distally from the dissecting tip to cut tissue distally adjacent to the dissecting tip. A sequencing element is mounted in the handle and operationally engaged with the first and second actuators. The sequencing element locks out movement of the second actuator between the central and proximal positions when the first actuator is in the open position.

Yet another aspect of the present invention is a method of using the above-described surgical instrument of the present invention to grasp and cut tissue.

The foregoing and other features and advantages of the present invention will become more apparent from the following description and accompanying drawings.

BRIEF DESCRIPTION OF THE DRAWINGS

FIG. 2 is an isometric view of the distal section of a tube assembly of the instrument of FIG. 1, shown with an upper jaw in an open position.

FIG. 3 is an isometric view of the distal section of the tube assembly of the instrument of FIG. 1, shown with the upper jaw in a closed position.

FIG. 7 is a side view of the interior of the handle assembly of the instrument of the present invention with the left handle shell removed, illustrating the actuators in positions to maintain the upper jaw in an open position and the cutting element in a central position.

FIG. 8 is a top view of the handle assembly of FIG. 7, with the left and right handle shell assembled.

FIG. 9 is a longitudinal, sectional view of the distal section of the tube assembly of FIG. 7.

FIG. 10 is a side view of the handle assembly of the instrument of the present invention with the left handle shell removed, illustrating the actuator positioned such that the upper jaw is in a closed position and the cutting element is in a central position.

FIG. 11 is a top view of the handle assembly of FIG. 10 with the left handle shell assembled with the right handle shell.

FIG. 12 is a longitudinal, sectional view of the distal section of the tube assembly of the instrument of FIG. 10.

FIG. 13 is a side view of the handle assembly of an instrument of the present invention having the left handle shell removed, showing the actuators located to cause the upper jaw to be in the closed position and the cutting element in a proximal position.

FIG. 14 is a top view of the handle assembly of FIG. 13, with the left handle shell assembled.

FIG. 15 is a longitudinal, sectional view of the distal portion of the tube assembly of the instrument of FIG. 13.

FIG. 16 is a side view of the handle assembly of the instrument of the present invention having the left handle shell removed, showing the acutators located such that the upper jaw is the closed position and the cutting element in a distal position.

FIG. 17 is a top view of the handle assembly of FIG. 16, with the left handle shell assembled.

FIG. 18 is a longitudinal, sectional view of the distal portion of the tube assembly of the instrument of FIG. 16.

BEST MODE FOR CARRYING OUT THE INVENTION

Figure 1:
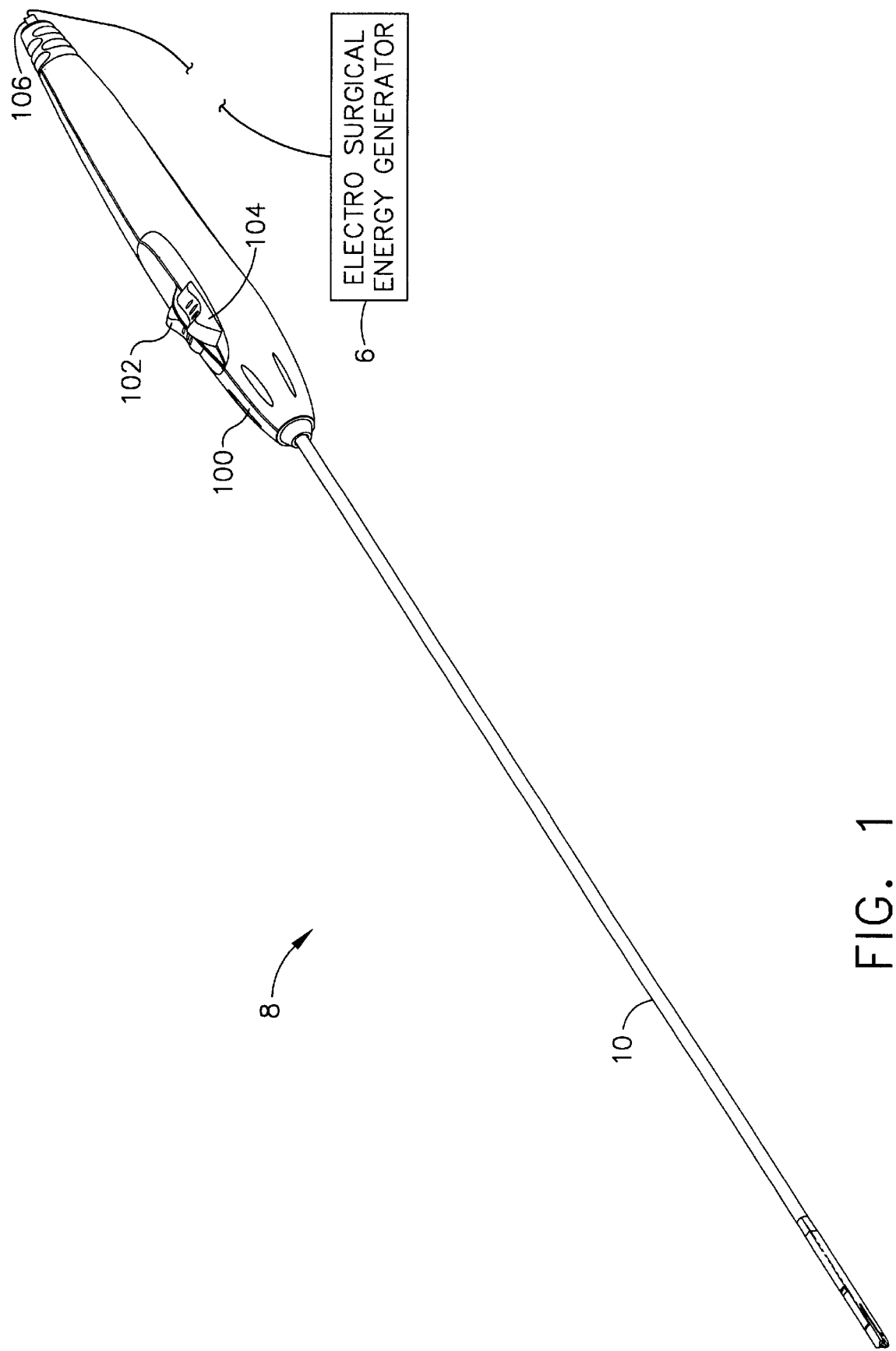
FIG. 1 is an isometric view of an electrosurgical clamping, coagulating, and cutting instrument of the present invention shown connected to a schematic of an electrosurgical energy generator.

The electrosurgical clamping, coagulating, and cutting instrument of the present invention is illustrated in FIG. 1 shown with a schematic representation of an electrosurgical energy generator 6. Instrument 8 is seen to have a handle assembly 100 and a tube assembly 10 having a distal end section and a proximal end. Handle assembly 100 is seen to be mounted to the proximal end of tube 10. Handle assembly 100 further comprises a first actuator 104, a second actuator 102, and a power cord 106 for electrical connection to electrosurgical energy generator 6. An operator actuates first actuator 104 for grasping and compressing tissue. The operator actuates second actuator 102 for cutting tissue. The operator presses a conventional foot switch (not shown) provided with electrosurgical generator 6 for supplying bipolar electrosurgical energy to instrument 8.

Instrument 8 operates with numerous conventional, commercially available, electrosurgical energy generators. An example of electrosurgical energy generator 6 is a unitary mono-polar-bipolar RF generator, such as the Valleylab "FORCE 2" RF Generator manufactured by Valleylab, a division of Tyco Healthcare Group LP, 5920 Longbow Drive, Boulder, Colo., 80301-3299, U.S.A.

Conventional power cord 106 may be long (for example, over two meters) and connect directly to electrosurgical energy generator 6 via standardized, bipolar connectors, which are well-known in the art. Power cord 106 may also be short (less than one third of a meter, for example) and have a standardized, conventional bipolar connection (also well-known in the art) to another, longer power cord, which is normally reusable and available with electrosurgical energy generator 6. An operator uses a foot-activated switch of electrosurgical energy generator 6 to supply energy through instrument 8 to the tissue being treated. The operator adjusts the maximum power setting on electrosurgical energy generator 6 to be in sufficiently effective range; for example a preferable range of approximately 20–60 watts, although instrument 8 operates at other conventional power settings also. The operator may press the foot switch and supply energy to instrument 8 for a few seconds to coagulate the tissue being treated. Only a portion (about 3 watts) of this energy is conducted through the tissue due to the high resistivity of tissue and the use of offset electrodes as described earlier and hereinafter. The operator may use instrument 8 to hemostatically seal a small (2–4 mm diameter) blood vessel, for example, in less than one second, but the operator may continue to depress the foot switch a few more seconds if desired since there is believed to be practically no additional, lateral spreading of thermal energy.

Referring now to FIG. 2, an isometric view of the distal portion or section of tube assembly 10 of FIG. 1 is illustrated. An elongated, closing tube 14 is shown retracted to an open position, holding upper jaw 42 in an open position relative to a stationary, opposing, lower jaw 44. Upper jaw 42 and lower jaw 44 are preferably injection molded from a biocompatible plastic such as polycarbonate or polyethylene or other conventional biocompatible polymeric materials. Closing tube 14 is preferably made from a stainless steel tube, although other conventional biocompatible materials may be used. The operator moves closing tube 14 in the proximal direction with respect to handle assembly 100 to open upper jaw 42 by moving first actuator 104 (see FIG. 1) in the proximal direction. The operator moves closing tube 14 in the distal direction to close upper jaw 42 by moving first actuator 104 in the distal direction.

Referring to FIGS. 2 and 3, closing tube 14 is shown to comprise a distal portion or section 18 and a proximal portion or section 16. Distal portion 18 of closing tube 14 is seen to have, preferably, an approximately rectangular, cross-sectional shape with a left surface 20, a right surface 21 (hidden), an upper surface 22, and a lower surface 23 (hidden), with surfaces 22 and 23 being curved as shown.

Tube 14 may have other geometric cross-sections such as circular, polygonal, oval, square and combinations thereof. Distal portion 18 of closing tube 14 further comprises distally extending upper arm 30 and lower arm 28 separated by a left slot 32 on left surface 20, and an identically shaped right slot 33 (hidden) on the right surface 21 (hidden). Proximal portion 16 of closing tube 14 slides freely inside of an elongated, tubular sleeve 12. Closing tube 14 and sleeve 12 are preferably constructed from round tubing in this embodiment, but may also be constructed from tubing having other geometric shapes such as, for example, rectangular, oval, polygonal, combinations thereof and the like. Although sleeve 12 may be made of a non-metallic material such as extruded polyethylene tubing, it is preferably metallic in order to contribute significantly to the bending stiffness of tube assembly 10. In this embodiment, tube assembly 10 is relatively long and thin (for example, fits through a 5 mm trocar) to enable the operator to use instrument 8 for endoscopic vessel harvesting as will be described.

Closing tube 14 is further seen to have a tab 26 formed into upper surface 22, which engages and opens upper jaw 42, as will be described for FIG. 9.

Still referring to FIGS. 2 and 3, upper jaw 42 is seen to have a plurality of upper teeth 58, and lower jaw 44 is seen to have a plurality of lower teeth 56, thus defining a tissue grasping region 57. Upper jaw 42 also includes an upper channel 54, and lower jaw 44 includes a lower channel 52, for the longitudinal movement of a cutting element 70 (see FIG. 4) partially contained inside of lower channel 52. A left fin 64 and a right fin 65 extend from lower jaw 44 to prevent cutting element 70 from cutting tissue when upper jaw 42 is in the open position. Upper jaw 42 further includes a blunt, upper tip 48 (also called a distal tip), and lower jaw 44 has a blunt, lower tip 46 (also called a distal tip). Upper tip 48 and lower tip 46 help the operator to funnel tissue into tissue grasping region 57. When upper jaw 42 is in the closed position, upper tip 48 and lower tip 46 form a V-shaped, dissecting tip 50 as shown in FIG. 3, which is useful for separating tissue layers as will be described. Upper arm 30 of closing tube 14 slides on a top surface 62 of upper jaw 42. Lower arm 28 of closing tube 14 slides on a bottom surface 60 of lower jaw 44. When lower jaw 42 is in the closed position as shown in FIG. 3, top surface 62 and bottom surface 60 are almost completely covered by closing tube 14. Tissue clamped between upper jaw 42 and lower jaw 44 extends laterally out of left slot 32 and right slot 33 (hidden) of closing tube 14, contacting a left lower edge 34 and a right lower edge 35 (see FIG. 4). A left flange 66 of upper jaw 42 separates tissue from a left upper edge 36 of upper arm 30. A right flange 67 (hidden) of upper jaw 42 separates tissue from a right upper edge 37 (hidden) of upper arm 30.

Figure 4:
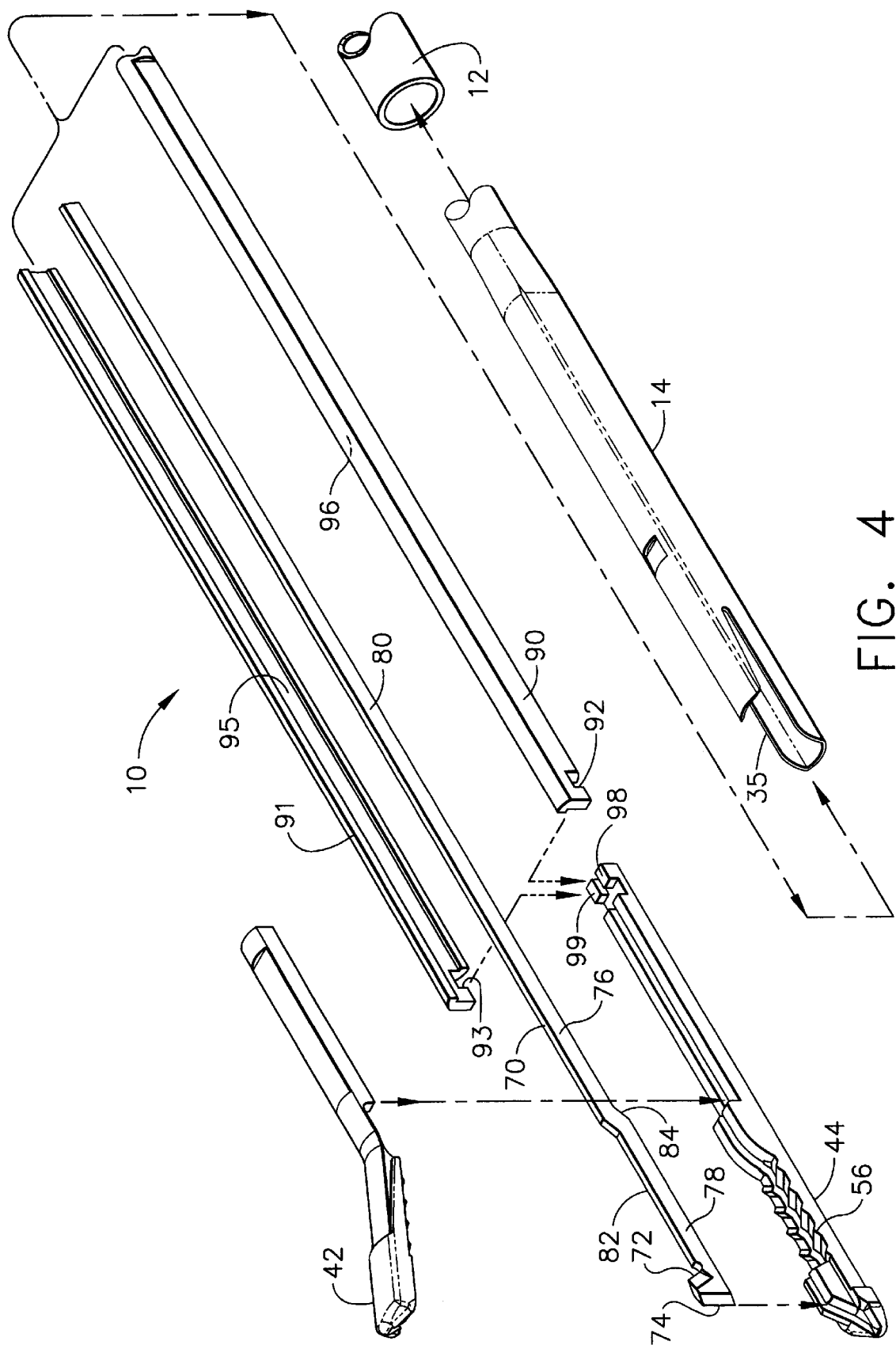
FIG. 4 is an exploded, isometric view of the distal section of the tube assembly of the instrument of FIG. 1.

Now referring to FIG. 4, an exploded, isometric view of the distal portion of tube assembly 10 is shown. Upper jaw 42 is seen to have a distal portion 55 and a proximal portion 53 joined together at a hinge 49. Hinge 49 is sometimes referred to as a "living hinge" since it is a thin, flexible area of the injection molded, upper jaw 42. Upper jaw 42 also includes a cam follower 47 located near hinge 49, and a lip 43 located on top surface 62. Lower jaw 44 includes a distal portion 59 and a proximal portion 51 joined together at a cam 45. Cam follower 47 of upper jaw 42 rides against cam 45 of lower jaw 44.

As seen in FIG. 4, cutting element 70 comprises a proximal portion 80 partially shown), a distal portion 78, joined together at an offset 84. Proximal portion 80 comprises a longitudinal element 76 and is attached to second actuator 102 shown in FIG. 1. Distal portion 78 and proximal portion 80 may be constructed from one piece of metal, or may be separate metallic elements joined together, for example, by a weld, mechanical connectors, rivets, pins, etc., and the like. Distal portion 78 is seen to have on the distal end a first blade 72 for cutting in the proximal direction and an opposed second blade 74 for cutting in the distal direction. The blades may be made as part of the distal portion 78 or mounted thereto by conventional methods such as welding, rivets, mechanical fasteners, etc. Lower jaw 44 contains cutting element 70 in lower channel 52 so that edge 82 of cutting element 70 is approximately flush with lower teeth 56. Proximal portion 80 of cutting element 70 is slideably contained in a right channel 95 of a right retainer 91, and in a left channel 96 (hidden) of a left retainer 90. Left and right retainers, 90 and 91, are also referred to together as a shaft having a proximal and a distal end. Closing tube 14 slides freely over left retainer 90 and right retainer 91, which are mounted to handle assembly 100 of FIG. 1. Right retainer 91 and left retainer 90 are made from an electrically non-conductive material such as plastic, for example, in order to electrically isolate cutting element 70 from closing tube 14. As a secondary electrical barrier, cutting element 70 may also be coated as desired with an insulative material. An example of a suitable coating for cutting element 70 is a thin sufficiently effective (for example, about 0.005 mm), vacuum deposited polymer well known in the art as parylene-n (also referred to as parylene), which is based on a high purity raw material called di-paraxylylene. Edge 82 of distal portion 78 of cutting element 70 functions as an electrode surface and comes into contact with tissue held between upper jaw 42 and lower jaw 44. Edge 82 (also referred to as a second electrode surface) is not coated with parylene-n or any other insulating material, and is a conductive surface.

Still referring to FIG. 4, right retainer 91 is seen to include a right hook 93 extending distally from the distal end thereof for attachment to a right hook 99 extending proximally from proximal section 51 of lower jaw 44. Left retainer 90 includes a left hook 92 for engagement with a left hook 98 extending proximally from the proximal section 51 lower jaw 44. As a result, lower jaw 44 is stationary relative to cutting element 70 and closing tube 14. The operator actuates second actuator 102 to move cutting element 70 in either longitudinal direction, and actuates first actuator 104 to move closing tube 104 in either longitudinal direction. Upper jaw 42 moves a short distance during opening and closing in the longitudinal directions due to operational engagement with closing tube 14, as will be described.

Sleeve 12 fits concentrically over closing tube 14 and strengthens tube assembly 10 to resist bending as described earlier, and may be slidably mounted or fixedly mounted. Sleeve 12 also separates closing tube 14 from external structures rubbing against it that may impede its movement, such as tissue layers or a trocar seal if used with a trocar.

Figure 5:
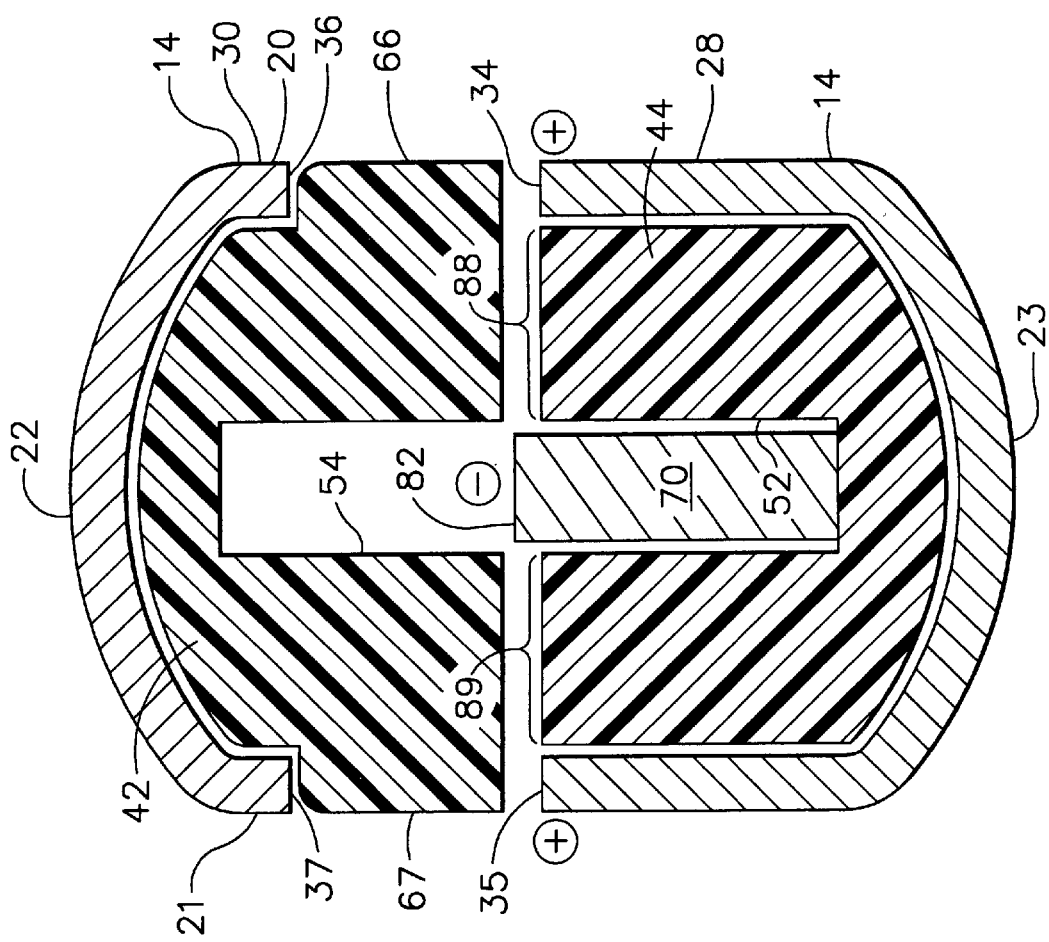
FIG. 5 is a cross-sectional view of the distal portion of the tube assembly taken through View-Line 5—5 of FIG. 3.

FIG. 5 is a cross-sectional view of the distal end of tube assembly 10 of FIG. 3, taken along View Lines 5—5. Left lower edge 34 (also referred to as a first conducting surface) and right lower edge 35 (also referred to as a second conducting surface) of lower arm 28 of closing tube 14 (also referred to as a first electrode) have a first polarity, for example, shown as positive. Spaced midway between left and right lower edges, 34 and 35, is edge 82 of cutting element 70 contained in lower channel 52 of lower jaw 44. Edge 82 has a second, opposite polarity, for example, shown as negative. Edge 82 is laterally offset and electrical isolated from left and right lower edges, 34 and 35. Therefore, edge 82 cannot electrically short to left and right lower edges, 34 and 35, if there is no tissue clamped between upper jaw 42 and lower jaw 44. However, bipolar electrosurgical current flows between edge 82 and left lower edge 34 through tissue clamped in a left compression zone 88 and bipolar electrosurgical current flows between edge 82 and right lower edge 35 through tissue clamped in a right compression zone 89. Tissue is coagulated simultaneously in both left compression zone 88 and right compression zone 89. Once this tissue is coagulated, tissue resistivity is increased and electrical conductivity is decreased. As a result, even though the operator may continue to supply bipolar electrosurgical energy to instrument 8 (by depressing the foot pedal control for the electrosurgical energy generator 6 of FIG. 1), it is believed that effectively no additional coagulation of tissue takes place. More significantly, there is no electrical pathway outside of the clamped jaws, 42 and 44. Therefore, there is effectively no lateral thermal spread and coagulation of tissue outside of the jaws, 42 and 44. Left upper edge 36 of closing tube 14 is electrically insulated from clamped tissue by left flange 66 of upper jaw 42. Right upper edge 37 of upper arm 30 of closing tube 14 is electrically insulated from clamped tissue by right flange 67 of upper jaw 42. First and second blades, 72 and 74, of cutting element 70 (see FIG. 4) extend into upper channel 54, to cut tissue contained between compression zones 88 and 89. Upper channel 54 also serves as a vent for vapor to escape from upper jaw 42 during the application of RF energy.

As seen in FIG. 5, closing tube 14 has a substantially rectangular cross-section formed by upper surface 22, lower surface 23, left surface 20, and right surface 21. The upper and lower surfaces 22 and 23 are seen to have a slightly curved configuration in a preferred embodiment. The rectangular cross-sectional configuration is believed to have several advantages over, for example, a circular cross-sectional configuration: the rectangular cross-sectional configuration allows upper arm 30 and lower arm 28 to be stiffer so that deflection of upper arm 30 and lower arm 28 is minimized when tissue is clamped between upper jaw 42 and lower jaw 44; the rectangular cross-sectional configuration allows better visualization of tissue structures on each side of closing tube 14; the rectangular cross-sectional configuration has a smaller footprint on the clamped tissue and allows a higher pressure to be applied to tissue for a given closing force applied, thus aiding in the formation of a hemostatic weld of the tissue.

The closing tube 14 is multifunctional in that it moves upper jaw 42 between the open and closed positions, and it also serves as an electrical conductor, with left and right lower edges, 34 and 35, being used as outer electrodes of the same polarity. Similarly, cutting element 70 is multifunctional in that it not only cuts tissue held between upper jaw 42 and lower jaw 44, but edge 82 of cutting element 70 serves as an electrode having opposite polarity of closing tube 14. By making closing tube 14 and cutting element 70 electrically active components, it is not necessary to provide separate, spaced apart, bipolar electrodes in lower jaw 44. Consequently, the overall width of lower jaw 44 is significantly smaller than would be if separate electrodes of opposite polarity were mounted in lower jaw 44. This enables the aforementioned benefits of a smaller footprint on the tissue. In addition, the number of components and the overall cost to manufacture the instrument is reduced by the multifunctionality of closing tube 14 and cutting element 70.

Because instrument 8 incorporates offset electrodes technology and the tissue reaches a high coagulation temperature only very briefly, tissue does not char or burn as may occur when using conventional bipolar instruments. Nevertheless, a small amount of sticking of tissue to electrode surfaces in instrument 8 may still occur. In instrument 8, closing tube 14 moves longitudinally (i.e., proximally or distally) for each time upper jaw 42 is opened or closed, thus causing the active electrical surfaces, right lower edge 35 and left lower edge 34, to move relative to the stationary tissue held between upper jaw 42 and lower jaw 44. This allows any tissue that may be adhering to right and lower edges, 34 and 35, after the application of energy and the coagulation of tissue, to break free. Similarly, each time the operator actuates cutting element 70 in either the proximal or distal direction, the electrically active surface, edge 82 of cutting element 70, breaks free from adhering tissue. All electrically active surfaces in instrument 8 are wiped against the tissue clamped for each cycle of operation (clamp/coagulate/cut/open), thus helping to keep those surfaces clean and electrically conductive. In addition, when the operator opens upper jaw 42, the ends of the treated tissue are more likely to fall freely from the jaws than if using conventional bipolar devices, and it is not necessary to excessively manipulate instrument 8 to remove the tissue.

Figure 6:
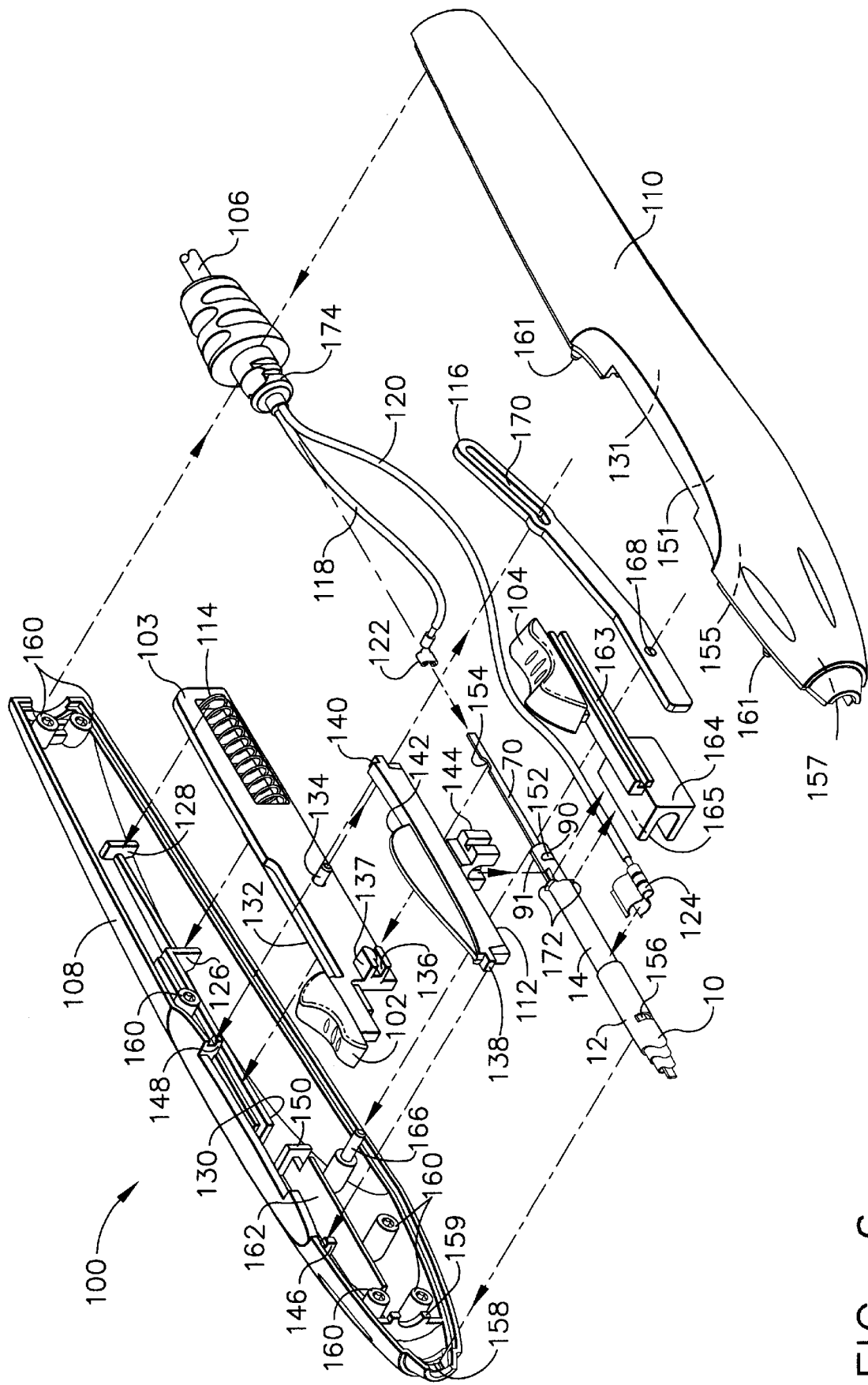
FIG. 6 is an exploded, isometric view of a handle assembly of the instrument of the present invention.

FIG. 6 is an exploded, isometric view of handle assembly 100, which preferably has an "in-line" style (as opposed to pistol-grip, etc.) in this embodiment, but is not restricted to this style. A right handle shell 108 includes a plurality of bosses 160 for assembly to a matching number of gripper pins 161 on left handle shell 110. Right and left handle shells, 108 and 110, are preferably injection molded from a rigid, conventional, biocompatible plastic such as polycarbonate and the like. The shells 108 and 110 support the following components: first actuator 104, second actuator 102, power cord 106, a divider 112, a bidirectional spring 114, and a sequencing lever 116 (also referred to as a sequencing element or operational sequencing element).

As described for FIG. 1, first actuator 104 is slidably mounted in handle assembly 100 and controls the longitudinal movement of closing tube 14 for opening and closing upper jaw 42 (FIG. 2). When the operator moves first actuator 104 distally from an open position to a distal closed position, upper jaw 42 closes. When the operator moves first actuator 104 proximally from the closed position to the open position, upper jaw 42 opens. First actuator 104 does not have a return spring or any other means for providing a biasing force to either the extended or open position in this preferred embodiment, although it is possible and within the scope of this invention to do so.

Second actuator 102 controls the longitudinal movement of cutting element 70. When the operator moves second actuator 102 in the proximal direction from a central position to a proximal position, first blade 72 (FIG. 4) of cutting element 70 moves proximally and cuts through tissue clamped between upper jaw 42 and lower jaw 44 within tissue grasping region 57 (FIG. 2). When the operator releases second actuator 102, it moves from the proximal position back to the central position due to the biasing force provided by bi-directional spring 114 (preferably a helical coil spring). As cutting element 70 moves distally from the proximal position to the central position, second blade 74 (FIG. 4) of cutting element 70 cuts a second time through tissue clamped between upper jaw 42 and lower jaw 44. When the operator moves second actuator 104 in the distal direction from the central position to a distal position, cutting element 70 extends distally so that second blade 74 (FIG. 4) is exposed to tissue adjacent to dissecting tip 50, allowing the operator to separate tissue layers and cut through tissue distally adjacent to dissecting tip 50 as the operator advances instrument 8 in the distal direction. When the operator releases second actuator 102, cutting element 70 moves proximally and again returns to the central position due to the biasing force provided by bi-directional spring 114. A biasing force is provided for cutting element 70 in this embodiment so that first and second cutting blades, 72 and 74, are safely contained between left and right fins, 64 and 65, of lower jaw 44 when the operator is not actuating second actuator 102. In another embodiment of the present invention, bi-directional spring 114 may be eliminated so that movement of the cutting element 14 is possible only when the operator moves second actuator 104.

Still referring to FIG. 6, second actuator 102 is seen to have a frame 103 that supports bidirectional spring 114, which is a helical coil wire compression spring in a preferred embodiment. If desired, other types of conventional springs may be used such as leaf springs, etc. A rail 132 on frame 103 of second actuator 102 rides inside of a right track 130 of right handle shell 108, so that bidirectional spring 114 is trapped between a first stop 126 and a second stop 128 of right handle shell 108. Second actuator 102 includes a mount member 136 having a projection 137 for insertion into and engagement with a notch 154 on cutting element 70, so that longitudinal translation of second actuator 104 causes an equal longitudinal translation of cutting element 70 in the same direction. First actuator 104 is seen to have a bar slider 163, which rides on a left track 131 (hidden) on the inside of left handle shell 110. First actuator 104 also has a closing block 164 that contains a pair of slots 165 (hidden) for receiving a pair of tabs 172 extending radially on the proximal end of closing tube 14, so that longitudinal translation of first actuator 102 causes an equal longitudinal translation of closing tube 14 in the same direction. Closing block 164 is supported and guided also by a right shelf 162 in right handle shell 108 and a left shelf 155 (hidden) in left handle shell 110. First actuator 104 and second actuator 102 are separated by divider 112 having a top fin 142 to help prevent the operator from actuating first and second actuators, 104 and 102, at the same time. Divider 112 also provides a tactile, positional reference for the operator to know the relative positions of first and second actuators, 104 and 102, without looking at them. A first tab 138 and a second tab 140 extending off opposite ends of divider 112 mount divider 112 to a first support 146 and a second support 148, respectively, of right handle shell 108. A yoke 144 on divider 112 mounts onto a right retaining fin 150 of right handle shell 108 and a similar, left retaining fin 151 (hidden) on the inside of left handle shell 110. First actuator 104, second actuator 102, and divider 112 are preferably injection molded from a rigid, biocompatible plastic such as polycarbonate, although many other conentional materials may also be used.

Still referring to FIG. 6, an optional, although preferred, sequencing lever 116 (also referred to as a sequencing element) ensures the proper sequence of operation of first and second actuators, 104 and 102. More specifically, sequencing lever 116 locks out second actuator 102 from moving to the proximal position (moving cutting element 70 to the proximal position) unless first actuator 104 is at the closed position (for when upper jaw 42 is closed and tissue is clamped). When tissue has been clamped for a period of time and electrosurgically coagulated, the tissue becomes less elastic and clamping force relaxes. To sever the coagulated tissue hemostatically, however, it is important that the coagulated tissue continue to be held firmly between upper and lower jaws, 104 and 102, so that cutting element 70 cuts through the middle of the coagulated tissue. This leaves an equal margin of coagulated tissue on each of the severed ends of the tissue so that the transection is hemostatic. Sequencing lever 116 also prevents first and second blades, 72 and 74, from being exposed to tissue in tissue grasping region 57 (FIG. 2) between upper and lower jaws, 42 and 44, while the operator positions instrument 8 prior to clamping, thus preventing inadvertent cutting of the tissue. Sequencing lever 116 also prevents first actuator 104 from moving from the closed position to the open position (to open upper jaw 42) unless second actuator 102 is safely in the distal or central positions and first and second blades, 72 and 74, are not in tissue clamping region 57. Sequencing lever 116 is preferably made of stainless steel, although it may be injection molded from a rigid, high strength plastic or other conventional materials. Sequencing lever 116 has a hole 168 that mounts pivotably onto post 166 of right handle shell 108, and a slot 170 for operational engagement with a first pin 134 extending off of frame 103 of second actuator 102.

FIG. 6 depicts a portion of power cord 106 having a strain reliever 174 that inserts between a pair of bosses 160 in right handle shell 108. Power cord 106 also includes an electrically insulated, first conductor 118 terminating with a first connector 122 for electrical attachment to cutting element 70, and an electrically insulated, second conductor 120 terminating with a second connector 124 for electrical attachment to closing tube 14. First and second connectors, 122 and 124, are shown in this embodiment to be configured for quick assembly, although various other types of connectors well known in the art or soldering and other conventional mounting techniques may be used in this application. The conductors are made from conventional conducting materials including copper wire, aluminum wire and the like and equivalents thereof.

Still referring to FIG. 6, it can be seen that handle assembly 100 retains tube assembly 10 as follows: left and right retainers, 90 and 91, have a pair of opposing recesses 152 for staking to left and right retaining fins, 151 (hidden) and 150. Sleeve 12 has a pair of opposing slits 156 (one is hidden) for retention in a right cradle 158 of right handle shell 108 and a left cradle 157 (hidden) of left handle shell 110. A holder 159 supports sleeve 12.

Now referring to FIG. 7, a side view of handle assembly 100 without left shell 110 reveals the orientation of sequencing lever 116 for when first actuator 104, attached to closing tube 14, is in the open position and second actuator 102 (substantially hidden by fin 142) is in the central position. First pin 134, which extends from frame 103 of second actuator 104 rests in slot 170 of sequencing lever 116. Closing block 164 of first actuator 104 prevents rotation of sequencing lever 116 about post 166, thereby causing slot 170 to be inclined relative to the longitudinal axis of handle assembly 100, and preventing movement in the proximal (right) direction of second actuator 102. As FIG. 7 shows, a lever end 117 cannot move in the clockwise direction until a closing block corner 169 is distal to it, thus preventing movement of second actuator 104 in the distal direction. Bi-directional spring 114 is slightly compressed within frame 103, but does not exert a biasing force on second actuator 102 in either longitudinal direction.

FIG. 8 is a top view of handle assembly 100 showing the positions of first actuator 104 and second actuator 102 (separated by fin 142) corresponding with FIG. 7.

FIG. 9 is a cross-sectional view of the distal portion of tube assembly 10, and corresponds with FIGS. 7 and 8. Closing tube 14 is in the open position so that tab 26 engages a lip 43 of upper jaw 42, causing a follower 47 of upper jaw 42 to ride up on a cam 45 of lower jaw 44, thus causing upper jaw 42 to flex at a hinge 49 of upper jaw 42 to the open position. Cutting element 70 is in the central position with first blade 72 and second blade 74 protected by left fin 64 (removed in this view) and right fin 65. When upper jaw 42 closes against lower jaw 44, cam 45 and left and right fins, 64 and 65, contain tissue to be clamped in tissue grasping region 57, ensuring that tissue to be treated does not squeeze out the distal end of the upper and lower jaws, 42 and 44, as may occur in other surgical grasping instruments. The wiping action of follower 47 against cam 45 also ensures that tissue is not pinched in between upper and lower jaws, 42 and 44, such as may occur in other surgical grasping instruments.

FIG. 10 is a side view of handle assembly 100 with left shell 110 removed to reveal the position of sequencing lever 116 for when first actuator 104 is in the closed position and second actuator 102 (substantially hidden by fin 142) is in the central position. Closing block corner 169 of closing block 164 is distal to lever end 117, thus allowing rotation of sequencing lever 116 about post 166, and proximal translation of second actuator 102. As first pin 134 extending off frame 103 translates proximally, slot 170 moves from the steeply inclined orientation shown in FIG. 10 to a less inclined position as shown in FIG. 13. Bi-directional spring 114 is in the same configuration for FIG. 10 as for FIG. 7, and is not providing a biasing force in either longitudinal direction to second actuator 104.

FIG. 11 corresponds with FIG. 10 and shows a top view of handle assembly 100 for when first actuator 104 is in the closed position and second actuator 102 is in the central position, with fin 142 between first actuator 104 and second actuator 102.

FIG. 12 is a sectional view of the distal portion of tube assembly 10 corresponding with FIGS. 10 and 11. Upper jaw 42 is in the closed position and tab 26 of closing tube 14 is separated from lip 43 of upper jaw 42. Follower 47 of upper jaw 42 abuts cam 45 of lower jaw 44 so that upper jaw 42 fits tightly against lower jaw 44 with very minimal air gaps there between. This ensures that tissue may be securely clamped during coagulation and cutting, and provides an additional electrical barrier between cutting element 70 and closing tube 14. First blade 72 and second blade 74 are in the central position and safely separated from tissue that may be clamped between upper jaw 42 and lower jaw 44. Dissecting tip 50 may be used in this configuration as a blunt dissector and tissue layer separator without cutting.

FIG. 13 is a side view of handle assembly 100 with left shell 110 removed to reveal the position of sequencing lever 116 for when first actuator 104 is in the closed position and second actuator 102 is in the proximal position. Fin 142 provides a tactile reference for the operator to feel the change of position for first and second actuators, 104 and 102. Closing block corner 169 of closing block 164 is distal to lever end 117 so that sequencing lever 116 rotates about post 166 when first pin 134 translates proximally within slot 170. Bi-directional spring 114 is compressed between frame 103 of second actuator 102 and second stop 128 of handle shell 108, thus providing a biasing force in the distal direction (and urging second actuator 104 to move from the proximal position to the central position.)

FIG. 14 is a top view of handle assembly 100 corresponding with FIG. 13 for when first actuator 104 is in the closed position and second actuator 102 is in the proximal position. Fin 142 separates first and second actuators, 104 and 102.

FIG. 15 is a sectional view of the distal portion of tube assembly 10 corresponding to FIGS. 13 and 14. Upper jaw 42 is in the closed position with closing tube 14 substantially covering upper jaw 42 and lower jaw 44. Cutting element 70 is shown in the proximal position with first blade 72 having made a first cut through tissue that may have been clamped between upper and lower jaws, 42 and 44. Second blade 74 is positioned to make a second pass through the tissue upon release of second actuator 104 (FIG. 13).

FIG. 16 is a side view of handle assembly 100 with left handle shell 110 removed and shows the position of sequencing lever 116 for when first actuator 104 is in the closed position and second actuator 102 (substantially hidden by fin 142) is in the distal position. Closing block corner 169 of closing block 164 is again distal to lever end 117, although this is not necessary for pin 134 to move in the distal direction inside of slot 170 of sequencing lever 116. Bi-directional spring 114 is compressed between first stop 126 of right handle shell 108 and frame 103 of second actuator 104, thus providing a biasing force to second actuator 104 in the proximal direction.

FIG. 17 is a top view of handle assembly 100 corresponding with FIG. 16, and shows first actuator 104 in the closed position. Fin 142 separates first actuator 104 from second actuator 102, which is in the distal position. The operator must hold second actuator 104 in the distal position due to the biasing force, which bidirectional spring 114 provides.

FIG. 18 is a sectional view of the distal portion of tube assembly 10, corresponding with FIGS. 16 and 17. Closing tube 14 surrounds upper jaw 42 and lower jaw 44 in the closed position. Cutting element 70 is in the distal position so that second blade 74 extends partially into the V-shape opening of dissecting tip 50 and is able to sever tissue that would be distally adjacent to dissecting tip 50. Second blade 72 is still protected within upper jaw 42 and lower jaw 44.

Figure 19:
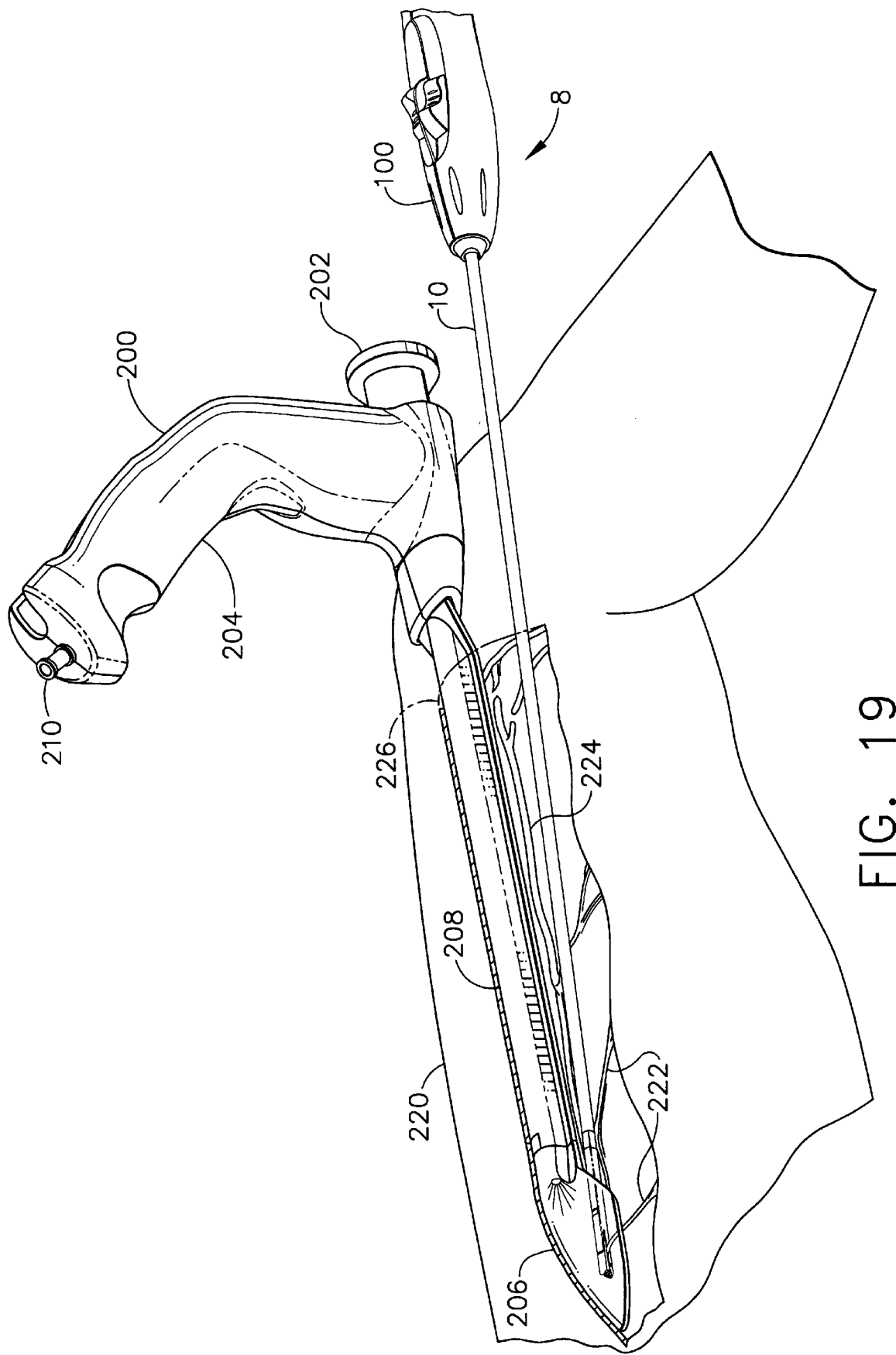
FIG. 19 is an isometric view illustrating the instrument of the present invention being used in combination with an endoscopic surgical retractor for surgically harvesting a vessel from a patient.

FIG. 19 is a isometric view of instrument 8 being used for a surgical procedure in combination with a surgical retractor 200 for endoscopically harvesting a vessel 224 from a surgical patient 220 for use in a coronary artery bypass graft (CABG) surgical procedure. Retractor 200 and its method of use are disclosed in U.S. Pat. Nos. 5,928,138 and 5,928,135 and are hereby incorporated herein for reference. Retractor 200 comprises a grip 204 attached to the proximal end of an endoscopic shaft 208, which may be inserted into an incision 226. A spoon element 206 is attached to the distal end of endoscopic shaft 208. The operator manipulates retractor 200 to advance a spoon shaped, working head 206 along vessel 224, separating tissue from vessel 224 and providing a working space for accessing and visualizing vessel 224 and a plurality of side branches 222. A port 202 provides access for an endoscope (not shown) for visualization within working head 206. A nozzle 210 may connect to a low pressure, carbon dioxide gas source for clearing away vapor and smoke from within the working space inside working head 206. Tube assembly 10 of instrument 8 inserts through incision 226 underneath shaft 208 of retractor 200. Tube assembly 10 could also be inserted through a port in an endoscope or retractor or endoscopic vein harvesting instrument. The operator manipulates instrument 8 within the working space inside working head 206 to dissect, clamp, coagulate, and cut tissue as described for FIGS. 7–18. In particular, side branches 222 are coagulated and cut without damaging harvested vessel 224. The length of tube assembly 10 may vary, but preferably is long enough for handle assembly 100 to be proximal to the endoscope inserts into port 202 while tube assembly 10 is inserted far enough into patient 220 to access the working space within working head 206. Instrument 8 may be used with other conventional retractors and vein harvesting instruments.

Instrument 8 is especially suited for vessel harvesting as described for FIG. 19, but is not limited to only this surgical procedure. Instrument 8 may also be used to dissect, clamp, coagulate, and cut tissues during numerous other types of endoscopic and open surgical procedures. Instrument 8, as described in the present embodiment, is intended for single patient use. Instrument 8 may be constructed, however, from materials and using techniques, allowing resterilization and reuse on more than one surgical patient.

Although this invention has been shown and described with respect to detailed embodiments thereof, it will be understood by those skilled in the art that various changes in form and detail thereof may be made without departing from the spirit and scope of the claimed invention.

What is claimed is:

1. A surgical instrument comprising:
   a) a handle having a distal end;
   b) a first actuator and a second actuator operably mounted to the handle;
   c) a shaft having a distal end, a proximal end, and having a lumen therethrough, the proximal end of the shaft mounted to the distal end of the handle;
   d) a first jaw and a second jaw mounted to the distal end of the shaft, the jaws each having distal ends being spaced apart when the first actuator is in an open position and being closer together for approximating tissue therebetween in a tissue grasping region when the first actuator is in a closed position;
   e) a cutting element operably connected to the second actuator and slidably disposed within the shaft, the cutting element comprising a first blade configured to cut tissue when the cutting element is moved proximally and a second blade configured to cut tissue when the cutting element is moved distally
   f) a sequencing element operationally engaged with the first and second actuators to prevent the second actuator from moving proximally when the first actuator is in the open position.

2. The surgical instrument of claim 1, comprising a centering spring operably connected to the cutting member for biasing the cutting member in a central position.

3. The surgical instrument of claim 1 wherein the sequencing element is adapted to lock the first actuator in the closed position when an operator moves the second actuator from the central position to the proximal direction.

4. The surgical instrument of claim 1, comprising at least two electrodes disposed on at least one of the first and second jaws, the electrodes adapted to contact tissue held in the tissue grasping region when the first actuator is in the closed position.

5. The instrument of claim 1, wherein the cutting element is configured to move in the proximal direction and the second blade to cut through tissue held in the tissue grasping region between the jaws when the second actuator moves from a central position to a proximal position.

6. The instrument of claim 5, wherein the cutting element is configured to move in the distal direction and the second blade to cut through tissue held in the tissue grasping region between the jaws when the second actuator moves from the proximal position to the central position.

7. The instrument of claim 5, wherein the cutting element is configured to move in the distal direction to extend the second blade distally from the first jaw and the second jaw when the second actuator moves from the proximal position to the central position.

8. A surgical instrument comprising:

a handle;

a first actuator and a second actuator operably mounted to the handle;

a first jaw and a second jaw operably connected to the first actuator, the jaws each having a distal end, the distal ends of the jaws being spaced apart when the first actuator is in an open position and the distal ends of the jaws being closer together for approximating tissue therebetween in a tissue grasping region when the first actuator is in a closed position;

a tube mounted to the handle;

a cutting element operably connected to the second actuator and slidably disposed within the tube; and a sequencing element operationally engaged with the first and second actuators, wherein the sequencing element prevents the cutting element from moving proximally when the first actuator is in the open position.

9. The surgical instrument of claim 8, wherein the sequencing element permits the cutting element to move distally when the first actuator is in the open position.

10. The surgical instrument of claim 8 comprising a centering spring operably engaged with the cutting element to bias the cutting element in a central position, and wherein the cutting element moves between a central position and a proximal position when the second actuator is moved proximally.

11. The surgical instrument of claim 8 wherein the cutting element comprises a first blade configured such that movement of the second actuator from a central position to a proximal position causes the first blade to cut tissue held in the tissue grasping region between the first jaw and the second jaw.

12. The surgical instrument of claim 11 wherein the cutting element comprises a second blade configured such that movement of the second actuator from the proximal position to the central position causes the second blade to cut tissue held in the tissue grasping region between the first jaw and the second jaw, and movement of the second actuator from the central position to a distal position causes the second blade to extend distally from a portion of the first jaw and the second jaw to cut tissue located distally adjacent to the first jaw and the second jaw.

13. The surgical instrument of claim 8, wherein the sequencing element is mounted within the handle.

14. The surgical instrument of claim 8, wherein the first jaw and second jaw are configured to form a dissecting tip when first actuator is in the closed position.

15. The surgical instrument of claim 8, comprising at least two electrodes disposed on at least one of the first jaw and the second jaw, the electrodes adapted to contact tissue held in the tissue grasping region when the first actuator is in the closed position.

16. The surgical instrument of claim 8, wherein the cutting element comprises a first blade configured to cut tissue when the cutting element is moved proximally and a second blade configured to cut tissue when the cutting element is moved distally.

17. The surgical instrument of claim 8, wherein the sequencing element permits the second actuator to move distally when the first actuator is in the open position.

18. A method of grasping and cutting tissue, the method comprising the steps of:

a. providing a surgical instrument comprising:
a handle;
a first actuator and a second actuator operably mounted to the handle;
a first jaw and a second jaw operably connected to the first actuator, the jaws each having a distal end, the distal ends of the jaws being spaced apart when the first actuator is in an open position and the distal ends of the jaws being closer together for approximating tissue therebetween in a tissue grasping region when the first actuator is in a closed position;
a tube mounted to the handle;
a cutting element operably connected to the second actuator and slidably disposed within the tube, the cutting element having a first blade configured to cut tissue when me cutting element is moved proximally and a second blade configured to cut tissue when the cutting element is moved distally; and
a sequencing element operationally engaged with the first and second actuators, wherein the sequencing element prevents the second actuator from moving proximally and permits the second actuator to move distally when the first actuator is in the open position;

b. cutting tissue at a location distal to the first jaw and the second jaw by moving the second actuator to a distal position to expose the second blade;

c. grasping tissue between the first jaw and the second jaw by positioning tissue between the first jaw and the second jaw and actuating the first actuator to grasp the tissue by approximating the first jaw and the second jaw; and d. cutting tissue between the first jaw and the second jaw by moving the second actuator proximally.

19. The method of claim 18, wherein the first blade cuts the tissue when the second actuator is moved proximally.

20. The method of claim 18, wherein the instrument comprises a biasing spring operably connected to the second actuator for biasing the second actuator to a central position, and wherein the first blade cuts tissue when the second actuator is moved proximally from the central position and the second blade cuts tissue when the second actuator is moved distally to the central position.

* * * * *